United States Patent [19]

Pegel

[11] 3,933,789

[45] Jan. 20, 1976

[54] EXTRACTION OF STEROLINS FROM PLANT MATERIAL

[75] Inventor: Karl Heinrich Pegel, Durban, South Africa

[73] Assignee: Roelof Wilke Liebenberg, Johannesburg, South Africa

[22] Filed: Mar. 5, 1973

[21] Appl. No.: 338,057

[30] Foreign Application Priority Data
Mar. 17, 1972 South Africa.................. 72/1855

[52] U.S. Cl................................ 260/210.5; 424/182
[51] Int. Cl.²........................................ C07J 9/00
[58] Field of Search................................ 260/210.5

[56] References Cited
UNITED STATES PATENTS
2,534,260    6/1949    Gisvold..................... 260/210.5

OTHER PUBLICATIONS

Osol, A. et al., United States Dispensatory–24 Ed.; 1947, p. 1607.

*Primary Examiner*—Lewis Gotts
*Assistant Examiner*—Cary Owens
*Attorney, Agent, or Firm*—Young & Thompson

[57] ABSTRACT

A method of obtaining a sterolin-rich product useful in the treatment of geriatric complaints such as benign hypertrophy of the prostate, comprising pulping a plant product containing sterolin, boiling the pulp in water, filtering the material thus obtained, and concentrating the filtrate to dryness, preferably at least in part by spray drying.

5 Claims, No Drawings

EXTRACTION OF STEROLINS FROM PLANT MATERIAL

THIS invention relates to a method of:
1. stabilising and/or
2. extracting sterolins from plant material (sterolins are phytosterol glycosides) including naturally occuring sterolin esters.

It has surprisingly been found that sterolins are an essential and useful food requirement and that these compounds are useful, if not essential, in the treatment of geriatric complaints and of so-called "civilisation" and old age diseases such as hypertrophy of the prostate gland, cholesterosis, arthritis, gout and the like. Thus unexpected therapeutic effects are obtained by oral administration of preparations or products containing such sterolins.

These sterolins are found in virtually all plants. They have been identified in applies (1), potatoes (2,3), carrots, onions, radish, lettuce (4), tobacco (5), cotton (6), peanuts (7), citrus fruit (8), spinach (9), beans (9) and others (11 – 15) and many more, but their therapeutic value or their importance as essential food constituent has up to the time of this invention never been recognised before (11, 16 – 20) although reports on their biological activity had appeared in the scientific literature (19, 21 – 23).

The products of this invention may be utilised as such as food products or therapeutic agents, or they may be used as additives or constituents of food products or pharmaceutical preparations. Since the beneficial value of these sterolin-enriched products depends on their sterolin content, this content determines the daily amount of product required by the consumer or patient (human or animal). Sterolins themselves are non-toxic when taken orally and it has been observed by the inventor that they are of little beneficial or therapeutic value when taken in pure crystalline form. It has been found that a daily dose of 0.01 mg. $\beta$-sitosteryl $\beta$-D-glucoside content (the most common natural phytosterolin) is adequate as a therapeutic measure. Overdoses of sterolins are harmless. Sterolin-enriched food products, food additives, pharmaceutical products or additives to pharmaceutical products should therefore aim at a preferred daily sterolin availability of 0.01 – 0.10 mg.

Sterolins obtained from any type of plant are better known as phytosterolins. These compounds are the glycosides, usually the glucoside of plant - or phytosterols. The most ubiquitous and abundant of these plant sterols is $\beta$-sitosterol (12, 24 – 27) usually accompanied by lesser amounts of campesterol and stigmasterol (24, 25, 26b) and very often small quantities of cholesterol (24, 25). The most abundant phytosterol and therefore phytosterolin in a plant or even a plant genus or family is not necessarily $\beta$-sitosterol and its glycosides (9, 12, 25, 27). Many other closely related phytosterols are known and they are all assumed and have been found to occur as the corresponding sterolins or esters thereof (1–3, 8, 9, 28–30). Occurrences (12, 15, 24, 25, 27, 31, 32) and descriptions (12, 15, 24, 25, 27, 31, 32, 33) of these plant sterols have been well documented.

It is an object of the present invention to provide a simple and efficient method of preserving, extracting or concentrating sterolins present in plant material, or alternatively, of preparing plant products in such a way that the natural sterolins are preserved from degradation or destruction.

Any sterolin preservation, extraction, enrichment or concentration process must first aim at the total destruction of all the glycosidic enzymes present in the plant material concerned. Glycosidic enzymes are relatively robust compounds that may be isolated by employing organic solvents (ethanol) as precipitating agent; only high temperatures (60° and higher) will permanently denature them. Thus temporary deactivation or denaturation through freeze-drying or organic solvent addition will not prevent a glycosidic enzyme from regaining its mode of action once the deactivating environment has been removed. Only after the glycosidic enzymes have been permanently denatured (destroyed) can the plant material be further processed for sterolin extraction, enrichment or concentration through its (the plant material) comminution followed by an aqueous boiling procedure. The preferred boiling period of the denatured aqueous plant pulp is from 30 minutes to 2 hours at either normal or elevated pressures.

According to the invention, a method is provided for the preservation, concentration and/or extraction of sterolins from plants containing them by:
a. deactivating the sterolin-specific degradative enzymes systems by heating the plant material (either as such or as pulps, shreds, slices, peels etc. obtained from plant parts).
b. the further processing of enzyme deactivated plant material to obtain sterolin rich concentrates or extracts by means of an aqueous boiling procedure.

This heating process may be applied to any plant material that is to be stored or further processed (e.g. pulping, juice extraction, drying, freezing and the like). It is important that this preserving process be applied at the earliest possible opportunity in any plant product manufacture, be it a food preserving, a sterolin extraction or a concentration procedure.

Applications of sterolin stabilisation in plant products are:
1. Heating of fresh plant material to deactivate sterolin specific degradative enzymes before processing commences to provide a final edible product.
2. Heating of plant products immediately after the first processing stages necessitating for example slicing, mincing, crushing, shredding, pulping, juice separation, etc. before further processing continues to provide final edible products.

The heating processes used for sterolin stabilization and, if required, sterolin mobilization may reach a final temperature of 60° – 200°C throughout the plant material whose enzymes have to be deactivated. The period of heating may range from seconds to hours since sterolins are relatively stable to heat under neutral conditions. Preferred heating times are 30 minutes to 1 hour when boiling commences if the final product is a sterolin enriched plant extract or concentrate, or 15 – 60 seconds at 75° ± 5°C when an enzyme destroying pasteurisation process for the preservation of sterolins is used. It will be appreciated that various forms of heating can be employed other than boiling such as, for example, steam heating or dry heating.

The plant material or product may consist of any finally edible non-poisonous or non-toxic plant product such as fruit of all types, leaves, stalks, roots and tubers etc. and even waste products such as peels, fruit pips, leaf waste etc.

Typical procedures according to the invention are as follows:

a. Plant material is heated immediately after comminution before further processing.
b. Plant material is heated before any plant cell damaging processes commence.

A useful and reliable test of sterolin activity is the therapeutic effect of sterolins on patients with benign hypertrophy of the prostate. This has been described in the U.K. Pat. Application No. 1 298 047.

EXTRACTION PROCEDURES

A comparison of various methods of extraction employed and the resultant sterolin concentration in a final sterolin enriched product gives a very good indication of the effectiveness of these different methods. In addition, the beneficial results of such enriched products when administered (in capsules and the like) to patients suffering from benign hypertrophy of the prostate gland indicates their therapeutic value and effectiveness.

Comparison of concentration of sterolins in extracts made from Hypoxis rooperi corms. The average quantity of sterolin contents calculated as Beta-sitosteryl B-D-glucoside obtained over a number of experiments, is expressed as mg. per 100 gram of spray-dried powder.

mg/100g.

Method 1(a):

The juice of 3 kilo washed Hypoxis corms was extracted by using a domestic juice extractor working on a centrifugal principle. The obtained juice filtered through finely woven cloth was refrigerated for 3 days and then spraydried.

0,035mg/100g.

Method 1(b):

The juice of 3 kilo washed Hypoxis corms was extracted by using a domestic juice extractor working on a centrifugal principle. The extracted juice was immediately poured into one liter of boiling water and the mixture boiled for 30 minutes. The mixture was then filtered through finely woven cloth and the filtrate refrigerated for 3 days before spraydrying it.

0,81 mg/100g.

Conclusion:
i. The difference in the concentration of the sterolin in both methods is attributed to the fact that the immediate boiling of the extracted juice stopped sterolin degradation by enzyme action.
ii. The boiling process extracted more of the sterolin from the fine fibres remaining in the extracted juice before they were removed by filtration in Method 1(b).

Method 2(a):

3 Kilo of fresh, washed Hypoxis corms were finely pulped and mixed with 6 liters of water at room temperature and left standing for 11 hours at room temperature before refrigeration was commenced. The mixture was then stored for 3 days in the cold before it was filtered and spraydried.

0,31 mg/100g.

Method 2(b):

3 Kilo of fresh, washed Hypoxis corms were finely pulped and mixed with 6 liters of water at room temperature and immediately refrigerated and stored for 3 days under refrigeration before being filtered and the filtrate spraydried.

5,75 mg/100g.

Method 2(c):

3 Kilo of fresh, washed Hypoxis corms were finely pulped and mixed with 6 liters of boiling water; boiling was continued for one hour. Thereafter the mixture was filtered and the filtrate refrigerated for 3 days before spraydrying.

8,92 mg/100g.

Conclusion:

It seems obvious that the very much increased concentration of the sterolin obtained in Methods 2(b) and 2(c) is due to the prevention of degradation of the sterolin through enzyme action as it must occur in Method 2(a) at room temperature for some time before refrigeration was started. The difference between 2(b) and 2(c) can be ascribed to:
i. partial sterolin degradation through enzyme action in Method 2(b);
ii. better and more complete extraction of the sterolin through continued aqueous boiling after pulping in Method 2(c).

Method 3(a):

3 Kilo of fresh, washed Hypoxis corms were finely pulped and mixed with 2.7 liters of absolute ethanol. The mixture was vigorously stirred for one hour, then filtered and the filtrate spraydried.

No measurable sterolin

Method 3(b):

3 Kilo of fresh, washed Hypoxis corms were finely pulped and mixed with 6 liters of a 60% ethanol-water mixture. The diluted pulp was vigorously stirred for one hour, filtered and the filtrate spraydried.

No measurable sterolin

Method 3(c):

3 Kilo of fresh, washed Hypoxis corms were finely pulped and mixed with 6 liters of a 60% alcohol-water mixture. The diluted pulp was refrigerated for 3 days, then filtered and the filtrate spray-dried.

0,23 mg/100g.

Conclusion:

The results of both Methods 3(a) and 3(b) indicate that a short period of extraction with either pure ethanol or an ethanol-water mixture does not extract or mobilise any sterolin and that a spray-drying procedure made no difference.

The higher concentration of sterolin recovered through a longer period of extraction under refrigerated conditions indicates that time plays a role in extraction with an ethanol-water mixture, but a comparison of Method 3(c) with Method 2(b) indicates that ethanol considerably reduces the amount of sterolin extracted over the same period, viz. 0,23 mg. compared to 5,75 mg. sterolin/100 g of final product.

Method 4(a):

3 Kilo of fresh, washed *Hypoxis rooperi* corms were placed in a closed container in a pressure cooker containing one liter of water. This was brought to boil at a pressure of 20 lbs. per square inch. Boiling was continued for 30 minutes. The autoclaved corms were then pulped through a homogeniser with continuous addition of a total of 6 liters of water. No further boiling was applied after this stage and the aqueous pulp was filtered. The spray-dried filtrate was essentially a water soluble carbohydrate rich powder.

Traces only

Method 4(b):

3 Kilo of Hypoxis rooperi corms were placed in a closed container in a pressure cooker containing one liter of water. This was brought to boil at a pressure of 20 lbs. per sq. inch. Boiling was continued for 30 minutes. The autoclaved corms were then pulped through a homogeniser with continuous addition of a total of 6 liters of water. The resulting pulp and water mixture was boiled for one hour after which it was strained and the filtrate sprayed-dried. The resulting light brown sterolin rich powder consisted essentially of soluble carbohydrates (sucrose, glucose, fructose and starches) and sterolins.

Conclusion: 9,01 mg/100g.

No efficient extraction of sterolin was achieved in Method 4 (a) although enzyme action had been eliminated by the high temperature used. The result of the additional boiling procedure in Method 4(b) after the pulp had been mixed with water indicates the necessity for this final hot (boiling) extraction procedure.

Therapeutic Effect A:

The products obtained from extraction methods 1(a), 1(b), 2(a), 3(a), 3(b), 3(c), and 4(a) showed no therapeutic effect when used on patients with benign hypertrophy of the prostate. The dosage used was 3 capsules per day, one after each major meal. Each capsule containing 100 mg. of the spray-dried powder, and the combined daily dose of sterolin was less than 0.01 mg. of sterolin in all cases.

Therapeutic Effect B:

The spray-dried powder obtained from extraction methods 2(b), 2(c) and 4(b) was used for the treatment of patients with symptoms of benign hypertrophy of the prostate. After two weeks' medication all the patients reported a subjective improvement of their symptoms. An examination after 4 weeks' treatment revealed that the volume of retained urine had decreased for all patients. On further prolonged treatment (3 months) a reduction in size of the swollen prostate gland was found.

Dosage:

3 capsules of the extract per day, one after each major meal. Each capsule contained 100 mg. of the extract with 0,005 mg. to 0,009 mg. of sterolin content (calculated as Beta-sitosteryl Beta-D-glucoside). This provided a daily effective dose of 0,015 mg. to 0,027 mg. of sterolin.

Method 5:

*Beta Vulgaris* L., subsp. varietas conditiva (the garden beetroot) roots treated and processed as in extraction method 4(b) provided a dark red powder with a sterolin content averaging 0,015% calculated as B sitosteryl B-D-glucoside.

Therapeutic effect:

Patients with symptoms of benign hypertrophy of the prostate were treated with the *Beta vulgaris* extract. The subjective and objective improvements of all patients were similar to those described under Therapeutic Effect B.

Dosage:

3 capsules of extract per day one after each major meal. Each capsule contained 50 mg. of extract with an average of ,0075 mg. of sterolin content. This provided a daily average dose of 0,0225 mg. of sterolin.

Method 6:

Potato peels are homogenised and the pulp directly introduced into boiling water and heating or boiling is continued for 30–60 minutes to effect sterolin extraction. The broth is filtered, the filtrate concentrated by boiling and the concentrate is finally spray-dried to yield a sterolin-rich extract.

I claim:

1. In a method for manufacturing a sterolin-rich product consisting essentially of the steps of, comminuting a plant material containing sterolins, and deactivating the sterolin-specific degradative enzymes systems by heating the material at a stage not later than immediately following comminution to a temperatuare of at least 60°C.: the improvement comprising extracting the sterolins from the comminuted material in aqueous solution by boiling the comminuted material in water for a continuous period of at least thirty minutes, separating the extract solution from the comminuted material, and concentrating the extract solution.

2. The method of claim 1 in which the heating step is performed immediately following comminution, the temperature of the material being raised rapidly to a level at least of the order of 60°C.

3. The method of claim 1 in which the heating and extraction steps coincide, the comminuted material being added to boiling water immediately following comminution.

4. The method of claim 1, in which the product is a powder, the concentration step comprising concentrating the extract solution to dryness.

5. The method of claim 4 in which the extract solution is spray-dried.

* * * * *